United States Patent
Suzuki

(10) Patent No.: US 8,440,130 B2
(45) Date of Patent: May 14, 2013

(54) MANUFACTURING APPARATUS AND MANUFACTURING METHOD FOR AN ABSORBENT BODY

(75) Inventor: Makoto Suzuki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/258,971

(22) PCT Filed: Feb. 18, 2010

(86) PCT No.: PCT/JP2010/052434
§ 371 (c)(1),
(2), (4) Date: Nov. 22, 2011

(87) PCT Pub. No.: WO2010/109988
PCT Pub. Date: Sep. 30, 2010

(65) Prior Publication Data
US 2012/0056357 A1     Mar. 8, 2012

(30) Foreign Application Priority Data
Mar. 24, 2009 (JP) .................................. 2009-072450

(51) Int. Cl.
*A61F 13/15* (2006.01)
(52) U.S. Cl.
USPC ........................................ 264/517; 425/80.1
(58) Field of Classification Search ........................ None
See application file for complete search history.

(56) References Cited

U.S. PATENT DOCUMENTS

| | | | |
|---|---|---|---|
| 5,004,579 A * | 4/1991 | Wislinski et al. ............. | 264/517 |
| 6,630,096 B2 * | 10/2003 | Venturino et al. ............. | 264/518 |
| 7,094,373 B2 * | 8/2006 | Heyn et al. .................... | 264/101 |
| 7,704,439 B2 * | 4/2010 | Matos et al. ................... | 264/511 |

FOREIGN PATENT DOCUMENTS

| | | |
|---|---|---|
| JP | 4-161153 A | 6/1992 |
| JP | 2000-178866 A | 6/2000 |
| JP | 2002-272782 A | 9/2002 |
| JP | 2004-222774 A | 8/2004 |
| JP | 2008-231609 A | 10/2008 |

OTHER PUBLICATIONS

International Search Report from corresponding PCT application No. PCT/JP2010-052434 dated Apr. 27, 2010, 4 pages.
Chinese First Office Action from corresponding China application No. 201080013589.9 dated Feb. 28, 2013, 5 pages.

\* cited by examiner

*Primary Examiner* — Mary F Theisen
(74) *Attorney, Agent, or Firm* — Brinks Hofer Gilson & Lione

(57) ABSTRACT

The manufacturing apparatus includes: a mold member including a mold formed in a depressed shape on a predetermined face and moves along a first direction; a supply duct arranged at a predetermined position in the first direction that supplies air towards the predetermined face; a partitioned-space-forming member that is disposed at a position opposite to the supply opening forming an enclosed space; and an air intake duct. As the mold passes the supply opening, the air in the supply duct is sucked into the closed space and the liquid absorbent material in the air is deposited onto the mold. The suction opening of the air intake duct is arranged opposite to the predetermined face in the closed space. Concerning at least a portion that is included in the air intake duct and is housed in the closed space, a central-axis direction of the portion has a component parallel to a moving direction in which the mold is moving at a central position of the suction opening.

11 Claims, 9 Drawing Sheets

MANUFACTURING APPARATUS AND MANUFACTURING METHOD FOR AN ABSORBENT BODY

RELATED APPLICATION

The present application is a 35 U.S.C. §371 national stage filing of International Patent Application No. PCT/JP2010/052434, filed Feb. 18, 2010, to which priority is claimed under 35 U.S.C. §120 and through which priority is claimed under 35 U.S.C. §119 to Japanese Priority Patent Application No. 2009-072450, filed Mar. 24, 2009.

TECHNICAL FIELD

The invention relates to a manufacturing apparatus and manufacturing method for an absorbent body according to an absorbent article such as a disposable diaper, etc.

BACKGROUND ART

As an example of an absorbent article to absorb exudates such as urine, menstrual blood, or the like, a disposable diaper, a sanitary napkin, etc are used. These absorbent articles include an absorbent body 1 that is obtained by forming pulp fibers into a predetermined shape.

This absorbent body 1 is shaped by a fiber depositing apparatus 10a in a manufacturing line. FIG. 1A is a side view of the fiber depositing apparatus 10a shown in a partial cross-sectional view, and FIG. 1B is a cross-sectional view taken along line B-B in FIG. 1A.

The fiber depositing apparatus 10a includes a rotating drum 20 that rotates in a circumferential direction Dc. Openings of both ends of this rotating drum 20 in a width direction (a direction perpendicular to the paper surface in FIG. 1A) are closed covering with a pair of circular walls 25, 25. Thereby, a negative pressure chamber S0 is partitioned on the inner circumferential side of the rotating drum 20. Also, molds 21 having a depressed shape are disposed of an outer circumferential face 20a of the rotating drum 20. A bottom section 21a of each mold 21 has a large number of suction holes 22, through which the bottom section 21a communicates with the negative pressure chamber S0. In addition, on the outer circumferential face 20a of the rotating drum 20, a supply duct 31 discharges mixed air 3 in which pulp fibers 2 are entrained is arranged opposite.

Thus, when the mold 21 passes through the position of the supply duct 31 with rotation of the rotating drum 20, the mixed air 3 that is discharged from the supply duct 31 is sucked into the bottom section 21a of the mold 21. In conjunction with this, the pulp fibers 2 in the mixed air 3 are deposited in the mold 21 and the absorbent body 1 is formed.

As shown in FIG. 1A, negative pressure in the negative pressure chamber S0 located on the inner circumferential side of the rotating drum 20 is generated by sucking air from the negative pressure chamber S0 with an air intake duct 41, which is connected to the circular wall 25. However, as shown in FIG. 1B, the air intake duct 41 is generally connected to only one wall 25 of a pair of the circular walls 25, 25 which is disposed in the width direction. Therefore, the suction pressure distribution in the mold 21 becomes uneven in the width direction of the rotating drum 20. This makes the deposit distribution of the absorbent body 1 in the mold 21 uneven in the width direction. In an example of FIG. 1B, deposits is thicker on the left portion to which the air intake duct 41 is connected, but deposits is thinner on the right portion which is an opposite site in the figure.

In terms of this, the Patent Literature 1 discloses that in order to prevent the suction pressure distribution from being uneven in the width direction, the suction pressure distribution in the width direction is adjusted by adjusting the extending length Ld of a suction opening 43d that is located on a pipe end of the air intake duct 41 as shown with double-dotted chained line in FIG. 1B, the suction opening 43d extending inwardly negative pressure chamber S0.

Citation List

[Patent Literature].

[PTL 1] Japanese Patent Application Laid-open Publication No. 2008-231609

SUMMARY OF THE INVENTION

Technical Problem

However, the extending length Ld which enables the suction pressure distribution to be even in the width direction differs depending on target basis weight ($g/m^2$) of the absorbent body 1 or production conditions such as rotational speed of the rotating drum 20. Therefore, every time these production conditions change, the extending length of the air intake duct 41 has to be adjusted, which is laborious.

The invention has been made in view of the above conventional problems, and an advantage thereof is to provide a manufacturing apparatus and manufacturing method for an absorbent body that definitely enables the deposit distribution to be even in the absorbent body without the foregoing adjustment of air intake duct.

Solution to Problem

An aspect of the invention to achieve the above advantage is a manufacturing apparatus for an absorbent body, including:

a mold member that includes a mold formed in a depressed shape on a predetermined face and moves the mold along a first direction intersecting a width direction of the predetermined face;

a supply duct that is arranged at a predetermined position in the first direction and supply air towards the predetermined face from a supply opening, the air containing a liquid absorbent material;

a partitioned-space-forming member that is disposed at a position opposite to the supply opening with the predetermined face in between, and that forms a partitioned closed space together with the predetermined face; and an air intake duct that sucks air in the closed space from a suction opening in order to set a pressure in the closed space to negative pressure, wherein when the mold passes a position of the supply opening, the air in the supply duct is sucked from a suction hole of a bottom section of the mold to the closed space and the liquid absorbent material in the air is deposited into the mold, and thereby the absorbent body is formed, the suction opening of the air intake duct is arranged opposite to the predetermined face in the closed space, and concerning at least a portion that is included in the air intake duct and is housed in the closed space, a central-axis direction of the portion has a component parallel to a moving direction in which the mold is moving at a central position of the suction opening.

Further,

A manufacturing method for an absorbent body, including:

preparing a mold member that includes a mold formed in a depressed shape on a predetermined face and moves the mold along a first direction intersecting a width direction of the predetermined face, a supply duct that is arranged at a predetermined position in the first direction and supply air towards the predetermined face from a supply opening, the air containing a liquid absorbent material, a partitioned-space-forming member that is disposed at a position opposite to the supply opening with the predetermined face in between, and that forms a partitioned closed space together with the predetermined face, an air intake duct that sucks air in the closed space from a suction opening in order to set a pressure in the closed space to negative pressure;

forming the absorbent body by a process in which, when the mold passes a position of the supply opening, the air in the supply duct is sucked from a suction hole of a bottom section of the mold to the closed space and the liquid absorbent material in the air is deposited into the mold, wherein the suction opening of the air intake duct is arranged opposite to the predetermined face in the closed space, concerning at least a portion that is included in the air intake duct and is housed in the closed space, a central-axis direction of the portion has a component parallel to moving direction in which the mold is moving at a central position of the suction opening.

Other features of this invention will become apparent from the description in this specification and the attached drawings.

Effects of the Invention

According to the invention, it is possible to definitely make the deposit distribution even in the absorbent body without the foregoing adjustment of air intake duct.

MODE FOR CARRYING OUT THE INVENTION

Figure 1A:
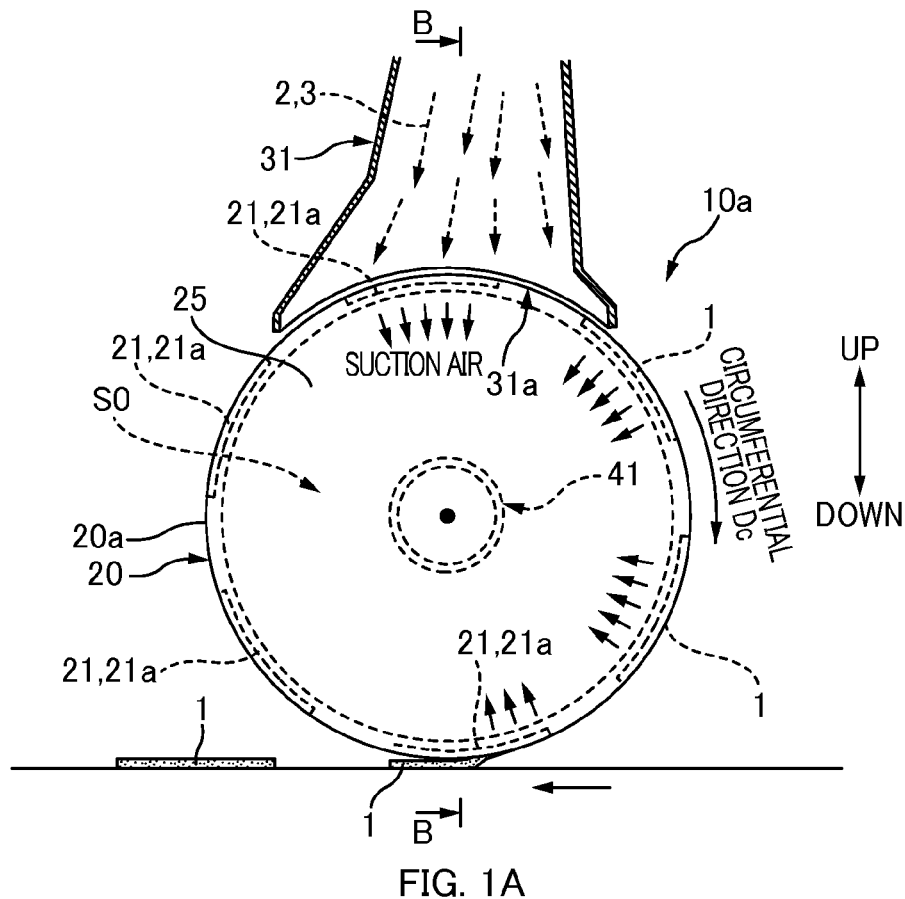
FIG. 1A is a side view showing a conventional fiber depositing apparatus 1a shown in a partial cross-sectional view.
Figure 1B:
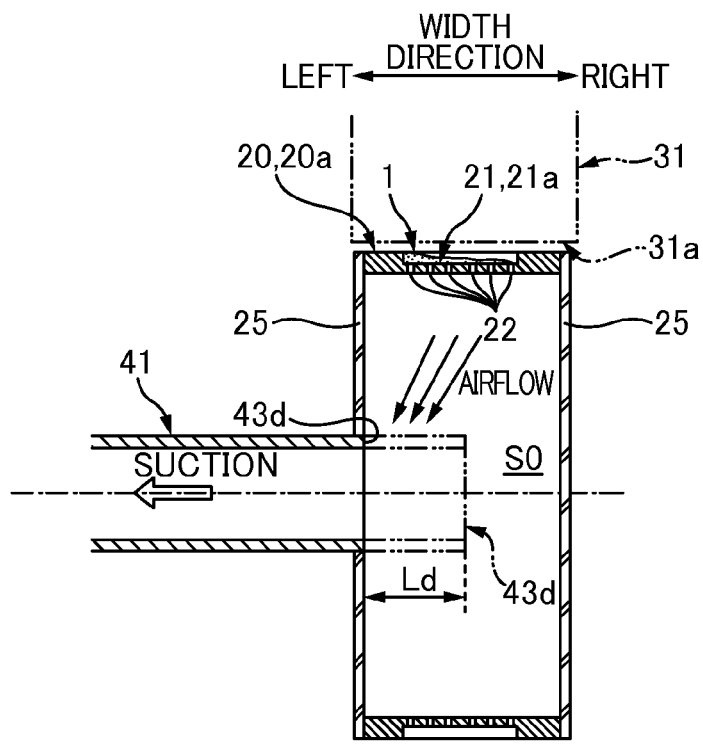
FIG. 1B is a cross-sectional view taken along line B-B in FIG. 1A.

At least the following matters will be made clear by the description in the present specification and the accompanying drawings.

A manufacturing apparatus for an absorbent body, including:

a mold member that includes a mold formed in a depressed shape on a predetermined face and moves the mold along a first direction intersecting a width direction of the predetermined face;

a supply duct that is arranged at a predetermined position in the first direction and supply air towards the predetermined face from a supply opening, the air containing a liquid absorbent material;

a partitioned-space-forming member that is disposed at a position opposite to the supply opening with the predetermined face in between, and that forms a partitioned closed space together with the predetermined face; and an air intake duct that sucks air in the closed space from a suction opening in order to set a pressure in the closed space to negative pressure, wherein when the mold passes a position of the supply opening, the air in the supply duct is sucked from a suction hole of a bottom section of the mold to the closed space and the liquid absorbent material in the air is deposited into the mold, and thereby the absorbent body is formed, the suction opening of the air intake duct is arranged opposite to the predetermined face in the closed space, and concerning at least a portion that is included in the air intake duct and is housed in the closed space, a central-axis direction of the portion has a component parallel to a moving direction in which the mold is moving at a central position of the suction opening.

In such a manufacturing apparatus for an absorbent body, the central-axis direction of the portion of the air intake duct has a component parallel to the moving direction in which the mold is moving at the central position of the suction opening. Further, the suction opening is opposite to the predetermined face including the mold. Therefore, between the portion and the suction opening, a bending section is formed by bending the central-axis direction of the pipe in a virtual plane that intersects with the width direction.

Even if, for instance, the suction pressure distribution of the portion is uneven in the width direction, the unevenness in the width direction is transformed by the bending section into the unevenness of the suction pressure distribution in the moving direction and is transmitted to the suction opening. This lessens the unevenness in the width direction, which results in even suction pressure distribution in the width direction in the mold.

In such a manufacturing apparatus for an absorbent body, desirably, a negative pressure source is included outside the closed space, the negative pressure source is connected to the portion from the width direction with a pipe in between, between the portion and the suction opening, a bending section is disposed, the bending section being formed by bending a central-axis direction of the pipe in a virtual plane that intersects with the width direction.

In such a manufacturing apparatus for an absorbent body, the unevenness of the suction pressure distribution in the width direction, which may be caused in the portion, is transformed by the bending section into the unevenness in the moving direction and is transmitted to the suction opening. This lessens the unevenness in the width direction, which results in even suction pressure distribution in the width direction in the mold.

In such a manufacturing apparatus for an absorbent body, desirably, the first direction is perpendicular to the width direction, between the portion and the suction opening, a bending section is disposed, the bending section being formed by bending the central-axis direction of the pipe in a virtual plane that is perpendicular to the width direction.

In such a manufacturing apparatus for an absorbent body, the unevenness of the suction pressure distribution in the width direction, which may be caused in the portion, is transformed into the unevenness in the moving direction by the bending section that is bent in the virtual plane parallel to the moving direction. And the unevenness is transmitted to the suction opening. This lessens the unevenness in the width direction which results in even suction pressure distribution in the width direction in the mold.

In such a manufacturing apparatus for an absorbent body, desirably, concerning a section of the air intake duct between the bending section and the suction opening, a central-axis direction of the section does not have a component in the width direction.

In such a manufacturing apparatus for an absorbent body, less unevenness in the width direction of the suction pressure distribution can be maintained.

In such a manufacturing apparatus for an absorbent body, desirably, the central-axis direction of the portion does not have a component in the width direction.

In such a manufacturing apparatus for an absorbent body, the central-axis direction of the portion does not have a component in the width direction. This prevents the suction pressure distribution from becoming more uneven in the width direction.

In such a manufacturing apparatus for an absorbent body, desirably, a negative pressure source is included outside the closed space, the negative pressure source is connected to the portion from the width direction with a pipe in between, the portion is formed extending towards a direction parallel to the moving direction, the portion is connected to a duct portion from the direction parallel to the moving direction, the duct portion including the suction opening, a central-axis direction of the duct portion does not have a component in the width direction.

In such a manufacturing apparatus for an absorbent body, the portion is formed extending towards a direction parallel to the moving direction. In addition thereto, the portion is connected to the duct portion including the suction opening from the moving direction. Further, the central-axis direction of the duct portion does not have a component in the width direction. This makes definitely the suction pressure distribution of the mold even in the width direction.

In such a manufacturing apparatus for an absorbent body, desirably, the closed space includes, along the first direction, a plurality of positions at which the air intake duct can be installed opposite to the supply opening, among the plurality of installable positions, the suction opening of the air intake duct is placed in at least a most upstream position in the first direction.

In such a manufacturing apparatus for an absorbent body, making the most effective use of the air intake duct ensures even deposit distribution of the absorbent body in the width direction.

In such a manufacturing apparatus for an absorbent body, desirably, the mold member is a rotating drum that continuously rotates in a circumferential direction that serves as the first direction, the mold is formed in a depressed shape at a predetermined interval in the circumferential direction on an outer circumferential face of the rotating drum, the outer circumferential face serving as the predetermined face, and a pair of circular walls that covers openings of both ends of the rotating drum in the width direction is included as the partitioned-space-forming member, and the closed space is partitioned on an inner circumferential side of the rotating drum.

In such a manufacturing apparatus for an absorbent body, it is possible to effectively achieve an operation and effect according to the present invention.

In such a manufacturing apparatus for an absorbent body, desirably, between the portion and the suction opening, a constricted section whose pipe is constricted in the width direction is disposed.

In such a manufacturing apparatus for an absorbent body, unevenness of the suction pressure distribution in the width direction is smoothed out and lessened by the constricted section. This makes the suction pressure distribution of the mold even in the width direction.

In such a manufacturing apparatus for an absorbent body, desirably, the suction opening is arranged opposite to the supply opening of the supply duct with the predetermined face in between.

In such a manufacturing apparatus for an absorbent body, the evenness of the suction pressure distribution of the suction opening in the width direction has a more direct influence on the deposit distribution of the absorbent body in the mold, which results in definitely making deposit distribution of the absorbent body even in the width direction.

Further,

A manufacturing method for an absorbent body, including:

preparing a mold member that includes a mold formed in a depressed shape on a predetermined face and moves the mold along a first direction intersecting a width direction of the predetermined face, a supply duct that is arranged at a predetermined position in the first direction and supply air towards the predetermined face from a supply opening, the air containing a liquid absorbent material, a partitioned-space-forming member that is disposed at a position opposite to the supply opening with the predetermined face in between, and that forms a partitioned closed space together with the predetermined face, an air intake duct that sucks air in the closed space from a suction opening in order to set a pressure in the closed space to negative pressure;

forming the absorbent body by a process in which, when the mold passes a position of the supply opening, the air in the supply duct is sucked from a suction hole of a bottom section of the mold to the closed space and the liquid absorbent material in the air is deposited into the mold, wherein the suction opening of the air intake duct is arranged opposite to the predetermined face in the closed space, concerning at least a portion that is included in the air intake duct and is housed in the closed space, a central-axis direction of the portion has a component parallel to moving direction in which the mold is moving at a central position of the suction opening.

In such a manufacturing method for an absorbent body, the central-axis direction of the portion of the air intake duct has a component parallel to the moving direction in which the mold is moving at the central position of the suction opening. Further, the suction opening is opposite to the predetermined face including the mold. Therefore, between the portion and the suction opening, a bending section is formed by bending the central-axis direction of the pipe in a virtual plane that intersects with the width direction.

Even if, for example, the suction pressure distribution in the width direction is uneven in the portion, the unevenness in the width direction is transformed by the bending section into the unevenness of the suction pressure distribution in the moving direction and is transmitted to the suction opening. This lessens unevenness in the width direction, which results in even suction pressure distribution in the width direction in the mold.

===Reference Example===

Figure 2A:
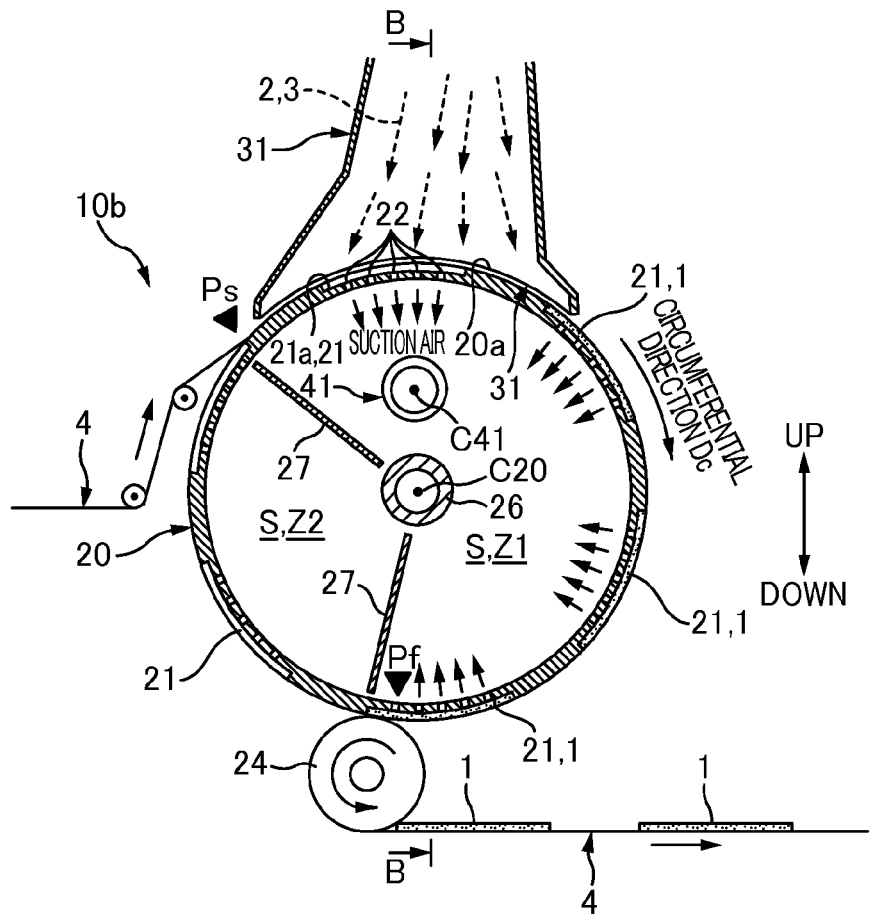
FIG. 2A is a longitudinal sectional view in the middle of the manufacturing apparatus 10b for the absorbent body 1 according to reference example.
Figure 2B:
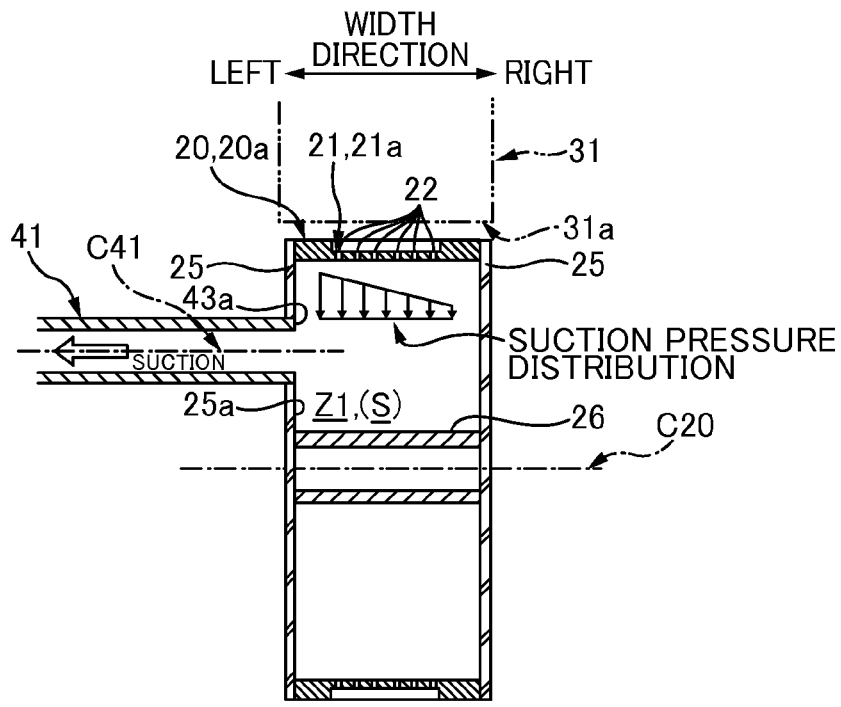
FIG. 2B is a cross-sectional view taken along line B-B in FIG. 2A.

FIG. 2A is a longitudinal sectional view in the middle of a manufacturing apparatus 10b for an absorbent body 1 according to reference example, and FIG. 2B is a cross-sectional view taken along line B-B in FIG. 2A.

The manufacturing apparatus 10b for the absorbent body 1 is a so-called fiber depositing apparatus that deposits pulp fibers 2 as a liquid absorbent material and forms the absorbent body 1. Indeed, its main components are: (1) a rotating drum (corresponding to a mold member) that continuously rotates about horizontal axis C20 in a circumferential direction Dc (for example, clockwise); and (2) a supply duct 31 that discharges and supplies mixed air 3 (corresponding to air) containing the pulp fibers 2 (corresponding to a liquid absorbent material) towards an outer circumferential face 20a of the rotating drum 20 from a supply opening 31a, the supply opening 31a being arranged at a predetermined position of the circumferential direction Dc of the rotating drum 20.

Hereinafter, the circumferential direction Dc of the rotating drum 20 is referred to as merely "the circumferential direction Dc", and a direction (a direction perpendicular to the paper surface in FIG. 2A) along the horizontal axis C20 of the rotating drum 20 is referred to as a "width direction" or "left-and-right direction". Therefore, the width direction and the circumferential direction Dc are perpendicular to each other.

The main body of the rotating drum 20 is a cylinder that rotates about the horizontal axis C20. Openings of the both ends of the rotating drum 20 in the width direction are covered and filled with a pair of circular walls 25, 25 (corresponding to partitioned-space-forming members). Further, a cylindrical wall 26 is formed inside the rotating drum 20 coaxially with the rotating drum 20; thereby a closed space S having a doughnut-shape is formed on an inner circumferential face of the rotating drum 20.

Further, the outer circumferential face 20a (corresponding to a predetermined face) of the rotating drum 20 is parallel to the width direction. Also, molds 21, which are in a corresponding depression shape to a shape of the absorbent body 1 to be formed, are formed intermittently at a predetermined interval in the circumferential direction Dc on the outer circumferential face 20a. A bottom section 21a of each mold 21 is also formed parallel to the width direction. On the bottom section 21a, a large number of suction holes 22 are formed, and communicate air-permeably with the inside of the mold 21 and the closed space S.

Further, as shown in FIG. 2A, the closed space S in the rotating drum 20 is divided by a partition wall 27 into a plurality of zones along the circumferential direction Dc. A first zone Z1 shown in the figure is connected to an air intake duct 41. Air in the first zone Z is sucked out from a suction opening 43a of the air intake duct 41, and inside of the first zone Z1 is maintained at negative pressure lower than the external pressure. Therefore, when the mold 21 passes the corresponding position to the first zone Z1 on the outer circumferential face 20a, air is sucked in from the suction holes 22 of the mold 21. However, a second zone Z2 is not connected to the air intake duct 41. Therefore, when the mold 21 reaches the corresponding position to the second zone Z2 on the outer circumferential face 20a, suction in the mold 21 almost ceases. In the first zone Z1, the supply opening 31a of the supply duct 31 is arranged. In the second zone Z2, a removal position Pf is set at which the absorbent body 1 is removed from the mold 21.

The supply duct 31 is arranged substantially above the rotating drum 20 and is a pipelike member having a substantially rectangular cross-section. The supply opening 31a, which is on the lower end of this supply duct 31, covers a portion that is substantially above the outer circumferential face 20a of the rotating drum 20, over a predetermined range. Further, from the upper end of the supply duct 31 (not shown), the pulp fibers 2 pulverized by a mill (not shown) etc is supplied with being entrained in airflow 3. Thereby, the mixed air 3 in which the pulp fibers 2 are entrained flows in the supply duct 31 towards the supply opening 31a located below. Depending on cases, it is possible that a polymer injection pipe (not shown) is included in the supply duct 31 to discharge and inject superabsorbent polymer towards the outer circumferential face 20a.

According to the fiber depositing apparatus 10b configured in this way, the absorbent body 1 is formed on a sheet-like member 4 such as nonwoven fabric etc, as follows. Firstly, as shown in FIG. 2A, at a position Ps of the circumferential direction Dc which is located upstream from the supply duct 31, the sheet-like member 4 is continuously supplied to the outer circumferential face 20a of the rotating drum 20 and is wrapped around the outer circumferential face 20a. The sheet-like member 4 on the outer circumferential face 20a does not slide on the outer circumferential face 20a and moves downstream of the circumferential direction Dc in conjunction with rotation of the rotating drum 20.

On the other hand, when the mold 21 on the outer circumferential face 20a passes the position of the supply duct 31 with rotation of the rotating drum 20, the mixed air 3 which is discharged from and supplied by the supply opening 31a is drawn into the suction holes 22 of the mold 21. However, at this time, passage of the pulp fibers 2 at the suction holes 22 are regulated by the sheet-like member 4 on the outer circumferential face 20a. Thus, on a portion that is of the sheet-like member 4 and abuts the bottom section 21a of the mold 21, the pulp fibers 2 in the mixed air 3 are deposited and the absorbent body 1 is formed. When the mold 21 has passed the position of the supply opening 31a and reaches the removal position Pf at which the outer circumferential face 20a faces downwards, the sheet-like member 4 is removed by a roller 24 from the outer circumferential face 20a, the roller 24 being arranged at the position Pf. Thereby the absorbent body 1 is removed from the mold 21 and is placed on the sheet-like member 4. With this, the absorbent body 1 is formed.

As the air intake duct 41 that is for setting the first zone Z1 of the rotating drum 20 to negative pressure, a pipe material whose pipe end 43a is open is generally used. The pipe-axis direction C41 of the air intake duct 41 is along the width direction of the rotating drum 20, and the air intake duct 41 is connected to either one wall 25 of the pair of circular walls 25, 25 associated with the rotating drum 20. The suction opening 43a, which is the pipe end 43a of the air intake duct 41, is arranged on the surface of an inner wall 25a of the circular wall 25.

However, this makes the suction pressure distribution within the mold 21 uneven in the width direction. Indeed, in an example of FIG. 2B, suction pressure of a left portion within the mold 21 becomes higher, and suction pressure of a right portion becomes lower. This makes deposit distribution of the absorbent body 1 uneven in the width direction; specifically speaking, the left portion of the absorbent body 1 which is deposited within the mold 21 is thick and the right portion is thin. Therefore, in order to prevent it, an air intake duct 50 is designed in the following first embodiment.

===First Embodiment===

Figure 3A:
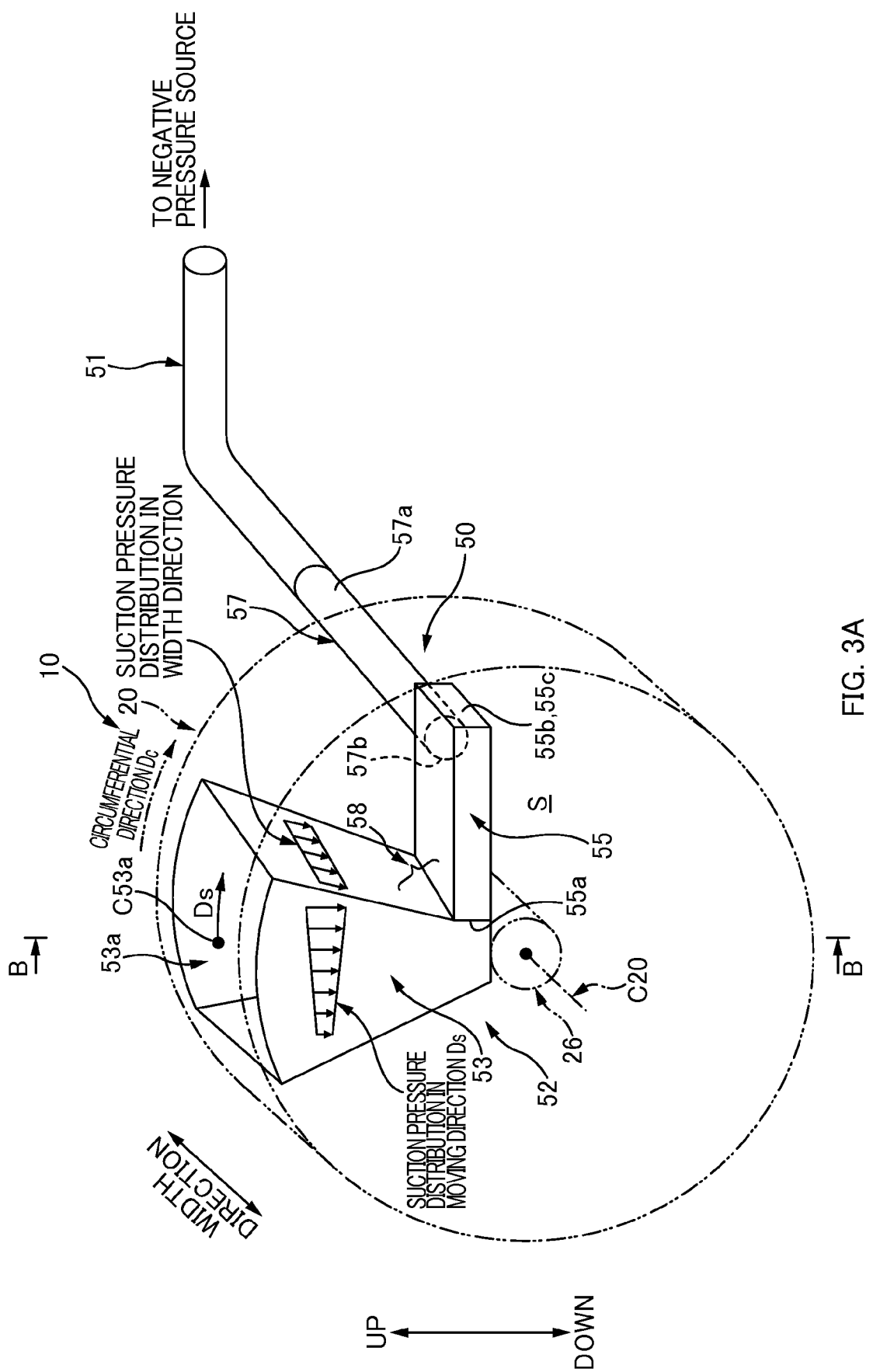
FIG. 3A is a perspective view schematically showing a manufacturing apparatus 10 for the absorbent body 1 according to the first embodiment.
Figure 3B:
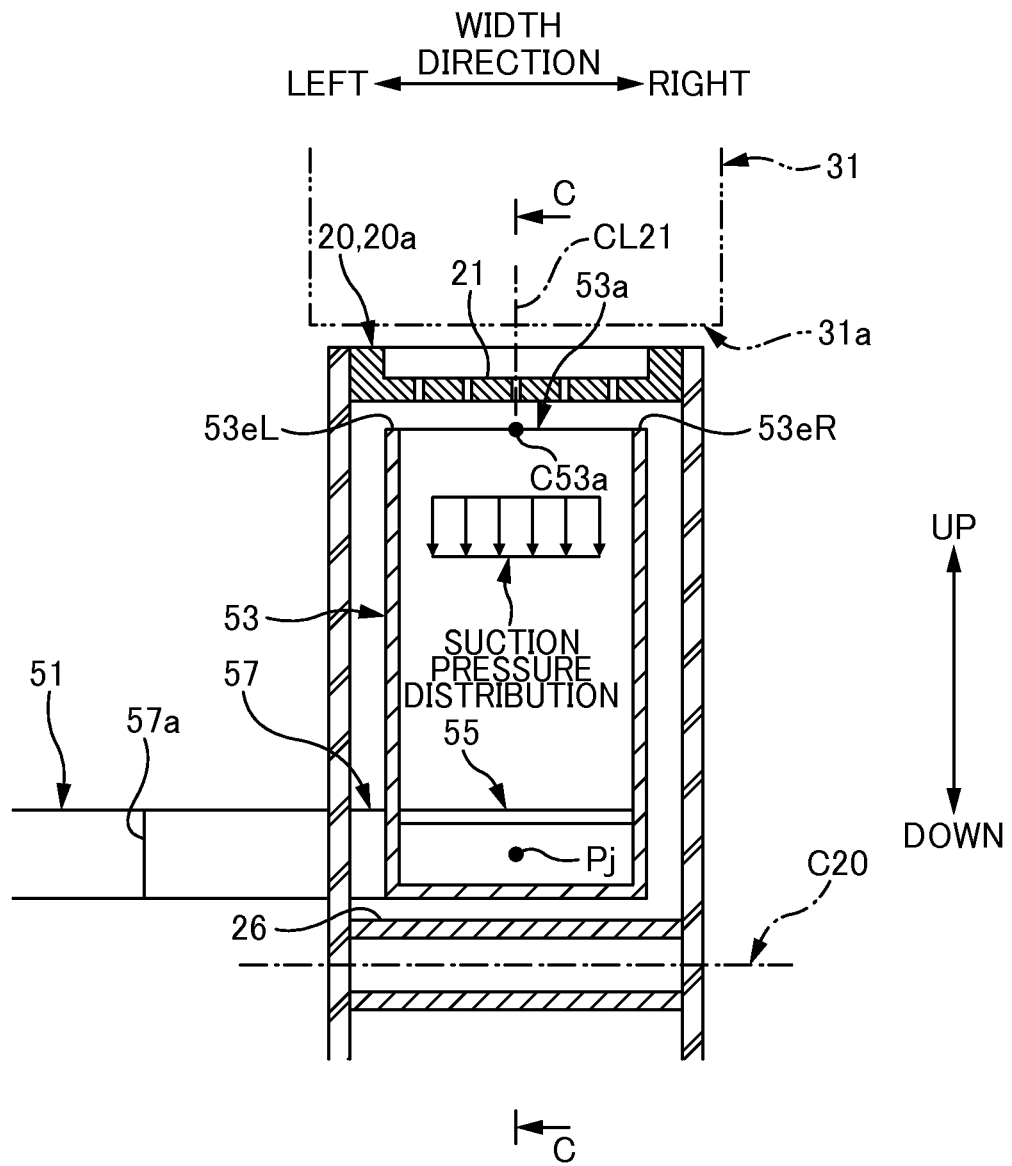
FIG. 3B is a cross-sectional view taken along line B-B in FIG. 3A.
Figure 3C:
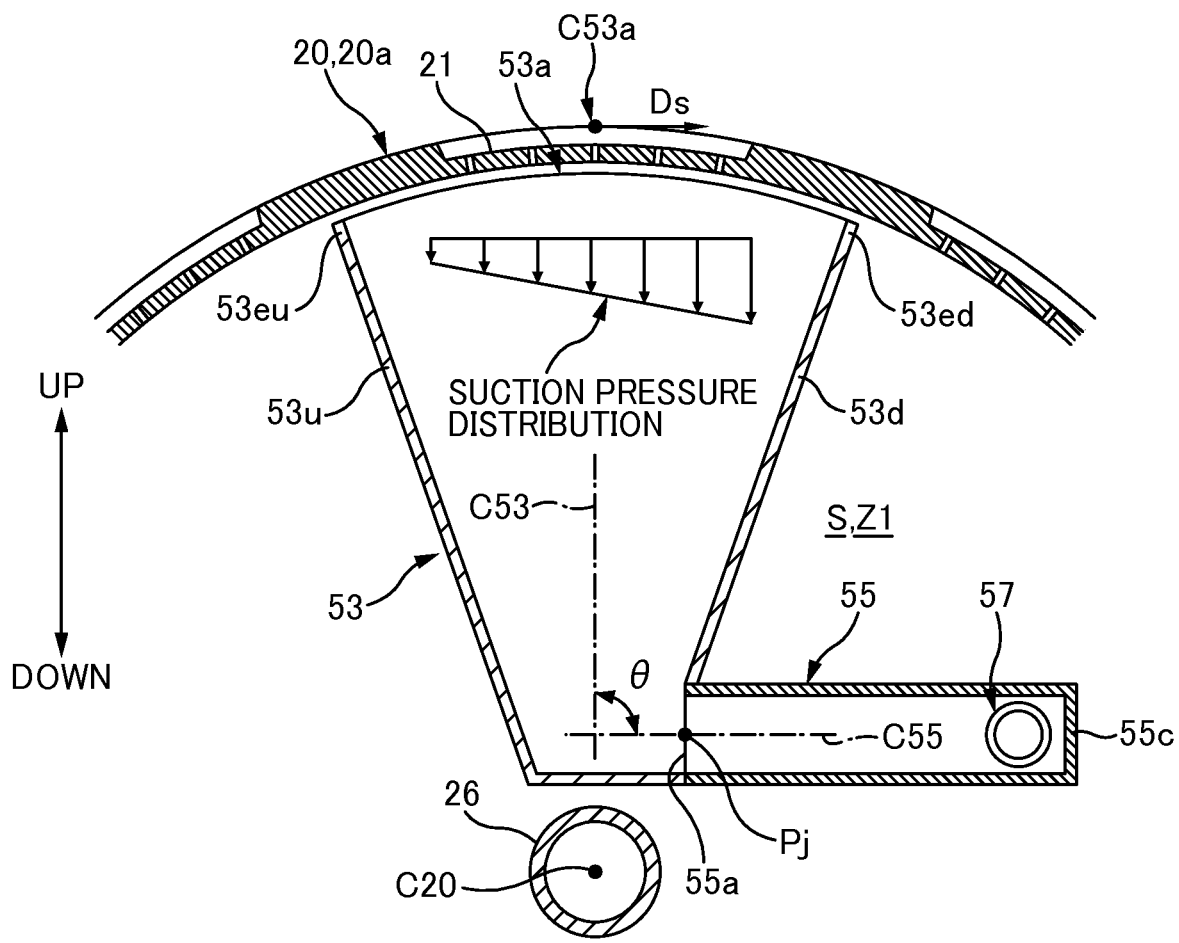
FIG. 3C is a cross-sectional view taken along line C-C in FIG. 3B.

FIGS. 3A to 3C are explanatory diagrams of a manufacturing apparatus 10 for the absorbent body 1 according to the first embodiment. FIG. 3A is a perspective view schematically showing the manufacturing apparatus 10, FIG. 3B is a cross-sectional view taken along line B-B in FIG. 3A, and FIG. 3C is a cross-sectional view taken along line C-C in FIG. 3B. In these figures, the same sign is used for the same configurations as the foregoing reference example, and description thereof is omitted. Further, in FIG. 3A, elements except for the air intake duct 50, such as the rotating drum etc, are shown by double-dotted chained line in order to avoid complications regarding the diagrams.

As shown with the solid line in FIG. 3A, the air intake duct 50 according to the first embodiment includes: an outside-rotating-drum duct portion 51 arranged outside the closed space S associated with the rotating drum 20; and an inside-rotating-drum duct portion 52 housed inside the closed space S.

The outside-rotating-drum duct portion 51 is connected, through a suitable pipe, to a negative pressure source (not shown) that is outside the rotating drum 20. The negative pressure source is a blower, vacuum pump etc, for example.

On the other hand, the inside-rotating-drum duct portion 52 includes: a suction box 53 having a suction opening 53a that is arranged opposite to the supply opening 31a of the supply duct 31 with the outer circumferential face 20a of the rotating drum 20 in between; a moving-direction duct portion 55 (corresponding to a "portion" in the claims) that is connected to the suction box 53 from a direction parallel to a moving direction Ds in which the mold 21 is moving at a central position C53a of the suction opening 53a; and a width-direction duct portion 57 that is connected to the moving-direction duct portion 55 from the width direction. A pipe end 57a of the width-direction duct portion 57 extends out of the rotating drum 20, and is connected to the foregoing outside-rotating-drum duct portion 51.

The suction box 53 is a pipelike member and its pipe-axis direction (the central-axis direction of the pipe, that is, it can be said that a direction along the line connecting the center point of every cross-section along the pipe) is facing substantially in the up-and-down direction. An upper pipe end is used as the suction opening 53a. A cross-sectional shape (a shape of a plane whose normal direction is the pipe-axis direction) of the pipe is substantially rectangular. In the rectangular cross-section, the length in the width direction is approximately constant throughout the length in the up-and-down direction, but the length in the moving direction Ds gets smaller as it goes from the upper end to the lower end. Thus, the pipe of the suction box 53 is substantially trumpet-shaped, which the pipe cross-sectional area of the lower end side is narrower than that of the upper end side. Further, in order to make the suction pressure distribution inside the mold 21 even in the width direction, the central position C53a of the suction opening 53a is approximately aligned with a center line CL21 of the mold 21 in the width direction (see FIG. 3B).

It is preferable that a pipe-axis direction of the suction box 53 does not have a component in the width direction, that is, the pipe-axis direction does not bend or incline in the width direction. In this example, the pipe-axis direction does not bend or incline in the width direction. This effectively prevents the suction pressure distribution in the suction box 53 from becoming more uneven in the width direction.

As shown in FIG. 3A, the moving-direction duct portion 55 is a suitable pipelike member, which is a square pipe having a rectangular cross-section in this example. Its pipe-axis direction is substantially parallel to the moving direction Ds in which the mold 21 is moving at the central position C53a of the suction opening 53a of the suction box 53. A pipe end 55a is connected to a lower end portion of the suction box 53 from a direction parallel to the moving direction Ds, and another pipe end 55b is closed with a suitable lid member 55c. To a neighboring portion of the other pipe end 55b, the width-direction duct portion 57 is connected, which will be described later.

It is preferable that pipe-axis direction of the moving-direction duct portion 55 does not have a component in the width direction. In other words, It is preferable that the pipe-axis direction does not bend or incline in the width direction. In this example, the pipe-axis direction does not bend or incline in the width direction. This effectively prevents the suction pressure distribution of the moving-direction duct portion 55 from becoming more uneven in the width direction.

The width-direction duct portion 57 is a suitable pipelike member; in this example, a round pipe having a round cross-section is employed. The pipe-axis direction thereof is substantially parallel to the width direction. A pipe end 57b is connected from the width direction to neighboring portion of the other pipe end 55b of the moving-direction duct portion 55. And, another pipe end 57a extends out of the rotating drum 20 and is connected to the outside-rotating-drum duct portion 51. Thus, the inside-rotating-drum duct portion 52 is coupled to the negative pressure source, and can undergo suction.

In this section, the description will be made regarding effects which the inside-rotating-drum duct portion 52 in the foregoing configuration achieves, that is, regarding making the suction pressure distribution of the suction opening 53a even in the width direction.

As mentioned above, the pipe-axis direction of the width-direction duct portion 57 is facing in the width direction. Therefore, as shown in comparative example of FIG. 4, in the case where the width-direction duct portion 57 is directly connected to the suction box 53, the suction pressure distribution of the suction opening 53a is uneven in the width direction, in the same way as the foregoing reference example.

However, as shown in FIG. 3A, in the first embodiment, between the suction box 53 and the width-direction duct portion 57, the moving-direction duct portion 55 is disposed. Further, the pipe-axis direction of that moving-direction duct portion 55 is facing in a direction parallel to the moving direction Ds in which the mold 21 is moving at the central position C53a of the suction opening 53a of the suction box 53. In addition thereto, the moving-direction duct portion 55 is connected to the suction box 53 from a direction parallel to the moving direction Ds. As a result thereof, between the suction box 53 and the moving-direction duct portion 55, a bending section 58 is formed whose pipe-axis direction is bent in a virtual plane perpendicular to the width direction.

Thus, the unevenness of the suction pressure distribution in the width direction is converted by the bending section 58 into the unevenness in the moving direction Ds, and is transmitted to the suction opening 53a. That is, as shown in FIGS. 3A and 3C, the suction pressure distribution inside the suction box 53 becomes uneven in the moving direction Ds, but instead thereof, the unevenness in the width direction is reduced (see FIGS. 3A and 3B). As a result, the suction pressure distribution of the suction opening 53a of the suction box 53 is less uneven in the width direction (see FIGS. 3A and 3B).

The detail is as follows. The unevenness of the suction pressure distribution of the suction opening 53a of the suction box 53 is caused depending on the connecting position of the duct portion at the suction box 53.

Figure 4:
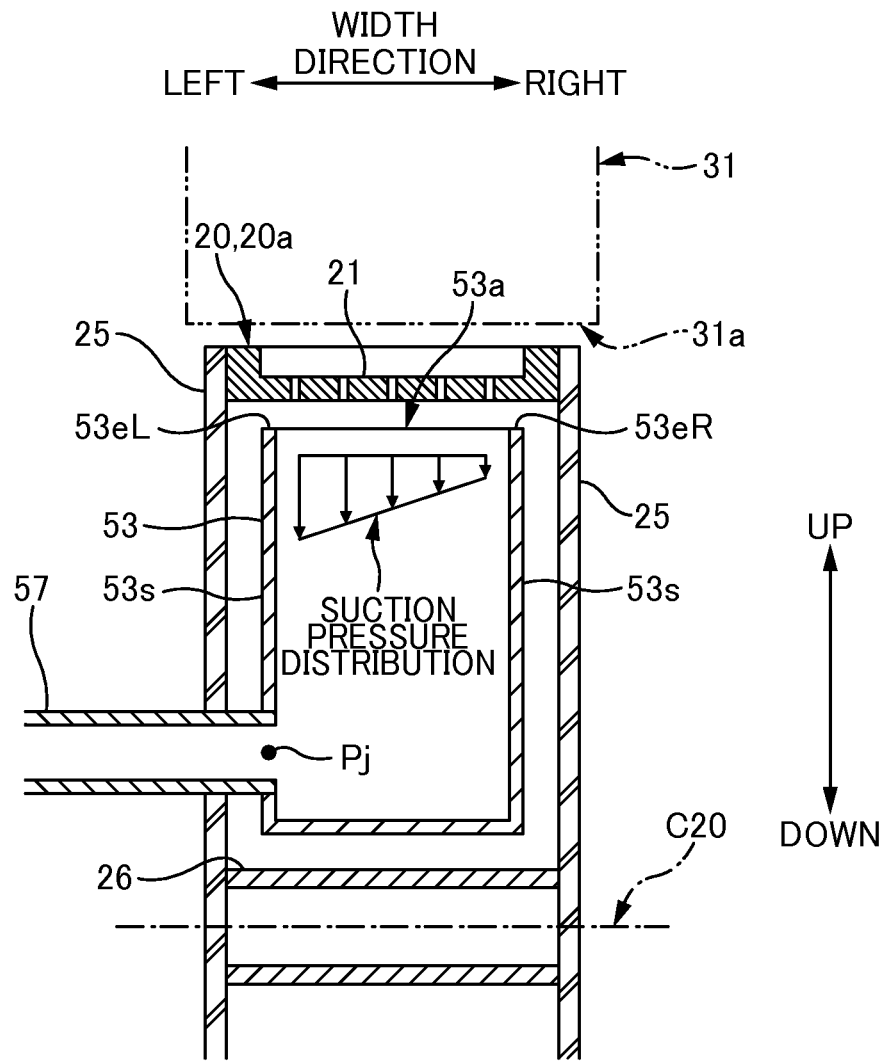
FIG. 4 is a cross-sectional view of a manufacturing apparatus of the comparative example.

For example, as the comparative example in the foregoing FIG. 4, in the case where the width-direction duct portion 57 is directly connected to the suction box 53, the width-direction duct portion 57 is along the width direction. Therefore, the width-direction duct portion 57 is connected to either one wall 53s(left wall 53s in the figure) of walls 53s, 53s, on the both side of the suction box 53 in the width direction. Then, the distance from the connecting position Pj to the right edge 53eR of the suction opening 53a in the width direction is different from the distance to the left edge 53eL thereof. As a result, depending on the difference between these distances, the suction pressure distribution of the suction opening 53a becomes uneven in the width direction.

As opposed thereto, as the first embodiment in FIG. 3A, in the configuration in which the suction box 53 is connected to the width-direction duct portion 57 with the moving-direction duct portion 55 in between, the moving-direction duct portion 55 is along the moving direction Ds. Therefore, as shown in FIG. 3C, the moving-direction duct portion 55 is connected to one wall 53d, of walls 53u, 53d on the both sides in the moving direction of the suction box 53. Then, as shown in FIG. 3B, the distance from the connecting position Pj to the left edge 53eL of the suction opening 53a in the width direction is equal to the distance to the right edge 53eR thereof. Therefore, unevenness of the suction pressure distribution in the width direction is reduced.

However, instead thereof, as shown in FIG. 3C, the distance from the connecting position Pj to the upstream edge 53eu of the suction opening 53a in the moving direction Ds is different from the distance to the downstream edge 53ed thereof. As a result, the suction pressure distribution is uneven in the moving direction Ds.

That is, concerning the suction pressure distribution inside the suction box 53, unevenness in the width direction is reduced. However, instead thereof, unevenness in the moving direction Ds increases. Further, in other words, it can be said that the unevenness of the suction pressure distribution in the width direction is transformed into the unevenness of the suction pressure distribution in the moving direction Ds, and is transmitted to the suction opening 53a of the suction box 53.

In the case where, as mentioned above, unevenness of the suction pressure distribution in the width direction is transformed into unevenness in the moving direction Ds to lessen and is transmitted to the suction opening 53a, it is sufficient that, as shown in FIG. 3A, the width-direction duct portion 57 is connected to the suction box 53 through the bending section 58 whose pipe-axis direction is bent in a virtual plane that is perpendicular to the width direction.

Further, although the following is slightly inferior in terms of making the suction pressure distribution even, it is also sufficient that the width-direction duct portion 57 is connected to the suction box 53 through the bending section 58 whose pipe-axis direction is bent in a virtual plane that intersects with the width direction.

In this regard, unevenness of the suction pressure distribution in the moving direction Ds shown in FIG. 3C does not constitute any problem with respect to deposits of the absorbent body 1. This is because all parts of the mold 21 in the moving direction Ds passes each point of the suction pressure distribution in the moving direction Ds in the same manner. Therefore, the unevenness has very small influence on deposit-thickness distribution in the moving direction Ds.

A bending angle θ (the angle θ between the pipe-axis direction C53 of the suction box 53 and the pipe-axis direction C55 of the moving-direction duct portion) of the bending section 58 shown in FIG. 3C is selected within the range in angle greater than 0° and smaller than 180°. It is preferable to select within the range in angle greater than 0° and smaller than and equal to 90°. It is more preferable to select within the range in angle greater than 0° and smaller than 90°. In the example of FIG. 3C, the bending angle θ is 90°.

Further, the central position of the bending section 58 in the width direction is almost the same as the central position C53a of the suction opening 53a of the suction box 53. This effectively prevents the suction pressure distribution from becoming more uneven in the width direction.

Figure 5:
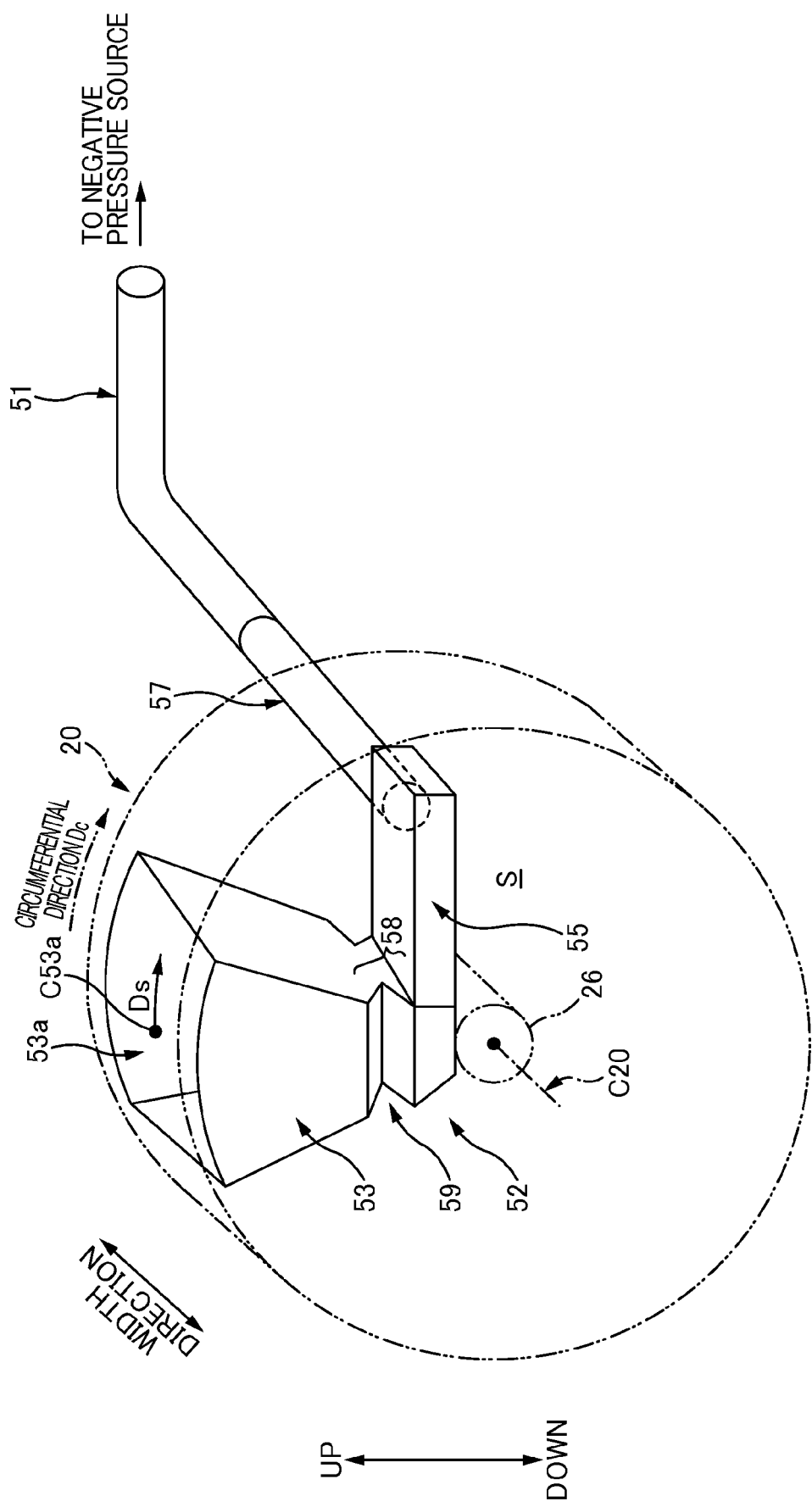
FIG. 5 is a perspective schematic view of an air intake duct 50 having a constricted section 59.

It is preferable that, as shown in perspective schematic view of FIG. 5, a constricted section 59 is disposed between the suction opening 53a of the suction box 53 and the moving-direction duct portion 55 and that the pipe is locally constricted in the width direction. In other words, it is preferable that the pipe of the constricted section 59 is narrower in the width direction than a portion adjacent to the constricted section 59 in the pipe direction. According to this, the suction pressure distribution which the bending section 58 has made even in the width direction is further smoothed out and lessened in the width direction by the constricted section 59. This can make the suction pressure distribution of the suction opening 53a of the suction box 53 more even in the width direction.

As a method for constricting the pipe, a method is provided in which the pipe narrows such that its cross-sectional shape is symmetric relative to the center line of the width direction, for example. This can prevent the unevenness of the suction pressure distribution from being induced in the width direction.

Such configuration examples of the constricted section 59, except for the configuration in which a pipe wall of the suction box 53 is constricted in FIG. 5, the following configurations are provided: a configuration in which a vane or plate (not shown) etc is arranged as a damper member in the pipe of the suction box 53 in FIG. 3A; a configuration in which a valve that opens, shuts, or partially obstructs an opening such as butterfly valve is arranged in the pipe, or the like. According to the latter configuration using a valve, there is an advantage that the degree of constriction in the width direction can be adjusted easily. Further, in the constricted section 59 in the example of FIG. 5, the pipe is constricted only in the width direction. However, in addition to this constriction in the width direction, the pipe may be constricted in a direction parallel to the moving direction Ds.

===Second Embodiment===

Figure 6A:
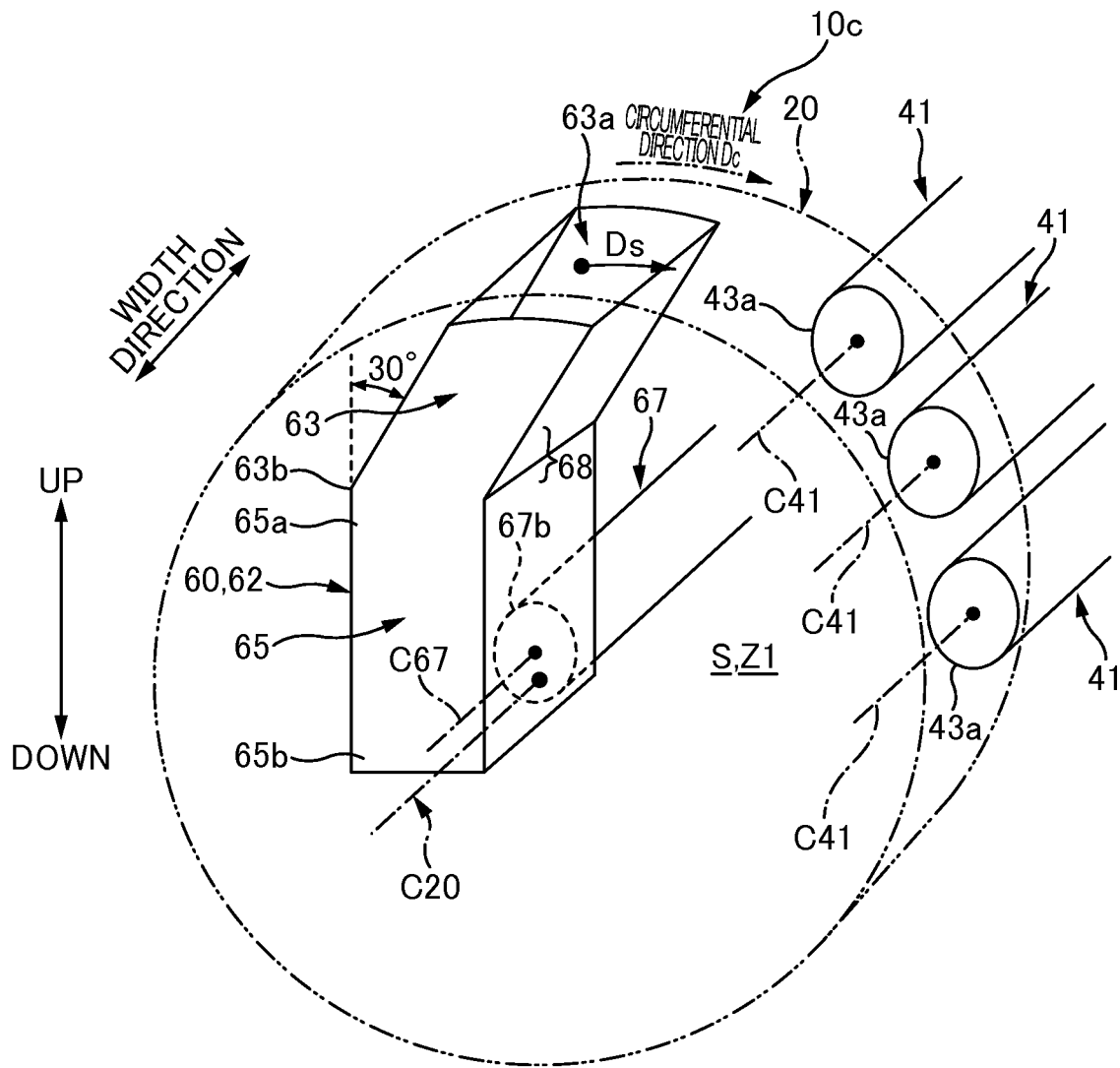
FIG. 6A is a perspective schematic view of a manufacturing apparatus 10c for the absorbent body 1 according to the second embodiment.
Figure 6B:
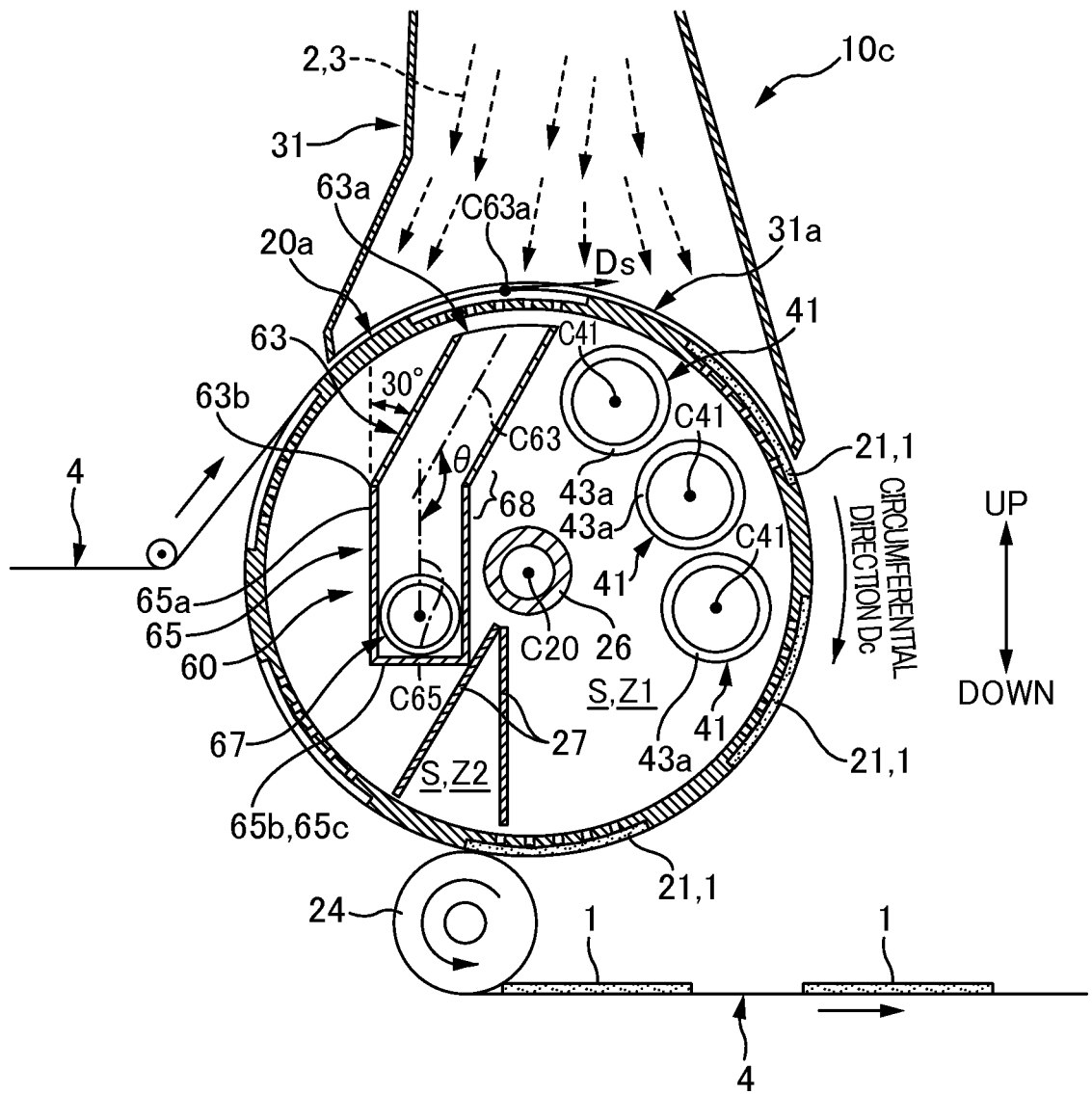
FIG. 6B is a longitudinal sectional view of the manufacturing apparatus 10c in the middle of the width direction.

FIGS. 6A and 6B are explanatory diagrams of a manufacturing apparatus 10c for the absorbent body 1 according to the second embodiment. FIG. 6A is a perspective schematic view of the manufacturing apparatus 10c, and FIG. 6B is a longitudinal sectional view of the manufacturing apparatus 10c in the middle of the width direction.

The second embodiment is different from the foregoing first embodiment in the following two points: a plurality of air intake duct 60, 41 are included; and a shape of air intake duct 60 is different. For aspects other than those described above, the second embodiment is substantially the same as the first embodiment. Therefore, the same elements are given the same reference numerals, and a description thereof and similar steps is omitted.

In the first zone Z1 of the rotating drum 20, four air intake ducts 60, 41, 41, 41 are disposed as an example of a plurality of air intake ducts. That is, in the first zone Z1, four positions at which air intake duct 60, 41 can be placed opposite to the supply opening 31a of the supply duct 31 are along the circumferential direction Dc of the rotating drum 20. In this example, air intake duct 60 according to the second embodiment is placed at only one position among these positions, and the air intake duct 41 of the reference example (FIGS. 2A and 2B) are used at the remaining three positions. This is because the air intake duct 60 according to the second embodiment requires a larger space to install than the air intake duct 41 according to the reference example and, by the constraint of free space because of this, the air intake duct 60 according to the second embodiment cannot be installed in all installable positions.

In this case, it is preferable that the air intake duct 60 according to the second embodiment is installed in the most upstream installable position on the circumferential direction Dc within the range of the drum that is opposite to the supply opening 31a. Further, if the space permits, it is preferable to enlarge the installation area by installing air intake ducts in the closest installable position on the downstream side so far as the position is within the range. This is because a primary deposit has greater influence than latter deposits on the deposit distribution of the suction pressure distribution of the absorbent body 1. Indeed, in the latter phase, as the depositing progresses to a certain degree, the deposit of the absorbent body 1 is thicker. Thus, pressure loss caused by the deposited absorbent body 1 becomes larger. As a result, even if there is variance of suction pressure distribution in the width direction, its influence on the deposit is reduced.

As shown in FIGS. 6A and 6B, the air intake duct 60 according to the second embodiment has an inside-rotating-drum duct portion 62 which is housed in the rotating drum 20, in the same way as the first embodiment. This inside-rotating-drum duct portion 62 includes: a suction box 63 having a suction opening 63a that is arranged opposite to the supply opening 31a with the outer circumferential face 20a of the rotating drum 20 in between; a vertical-direction duct portion 65 that is connected to the suction box 63 from vertically below; and a width-direction duct portion 67 that is connected to the vertical-direction duct portion 65 from the width direction.

The suction box 63 is a pipelike member whose pipe-axis direction is inclined from vertically above, at 30° for example in the moving direction Ds to be described later, in the same way as the first embodiment. The upper pipe end of the suction box 63 is used as the suction opening 63a. The cross-sectional shape of the pipe is substantially rectangular, and the rectangular cross-section is the same throughout the length. The moving direction Ds of the mold 21 is inclined slightly towards above with respect to the horizontal, at the central position C63a of the suction opening 63a.

The vertical-direction duct portion 65 is a pipelike member whose pipe-axis direction is facing in the vertical direction; in this example, a square pipe having a rectangular cross-section is used. An upper pipe end 65a is connected to a lower end 63b of the suction box 63 with engaging from below, and a lower pipe end 65b is closed with a suitable lid member 65c. To a neighboring portion of the lower pipe end 65b, the width-direction duct portion 67 is connected.

The width-direction duct portion 67 is a round pipe whose pipe-axis direction C67 is along the width direction in the same way as the width-direction duct portion 57 according to the first embodiment. One pipe end 67b is connected, from the width direction, to a neighboring portion of the lower pipe end 65b of the vertical-direction duct portion 65. The other pipe end (not shown) extends outside the rotating drum 20, and is connected to the outside-rotating-drum duct portion (not shown). Thereby, the inside-rotating-drum duct portion 62 is coupled to the negative pressure source, and can undergo suction.

The inside-rotating-drum duct portion 62 has a bending section 68 at a position at which the vertical-direction duct portion 65 is connected to the suction box 63. In other words, the inside-rotating-drum duct portion 62 bends, on the bending section 68, at the bending angle θ of 150° (angle θ between pipe axis C65 of the vertical-direction duct portion 65 and the suction box 63) according to the foregoing 30°. This bending is in the virtual plane perpendicular to the width direction. Therefore, in the same way as the foregoing first embodiment, unevenness of the suction pressure distribution in the width direction, which is caused by the width-direction duct portion 67, is transformed by the bending section 68 into unevenness in the moving direction Ds and is reduced. This makes the suction pressure distribution of the suction opening 63a even in the width direction.

In this regard, as a matter of course, concerning the three air intake ducts 41, it is possible to place the suction openings 43a of their pipe ends extending inwardly the rotating drum 20 and, thereby, to make the deposit more even.

===Other Embodiments===

Embodiments of the present invention have been described as above, however the present invention is not limited to these embodiments and the following variations are also possible.

In the foregoing embodiment, the rotating drum 20 is provided as a mold member. However, the invention is not limited thereto. For example, as a mold member, a belt of a belt conveyor can be employed. More specifically, firstly, the mold 21 is formed in a depressed shape on a belt surface (corresponding to a predetermined face) of the belt. The belt moves in a predetermined path. Also, the supply duct 31 is arranged at a predetermined position that is located on that path. In addition thereto, at a position opposite to the supply opening 31a of the supply duct 31 with the belt surface in between, a partitioned-space-forming member which forms a partitioned closed space together with the belt surface is disposed. The partitioned-space-forming member is a box which is for example a substantially rectangular parallelepiped in which a wall opposite to the belt surface is removed. For example, inside the closed space, a duct portion 52 of the air intake duct 50 in FIG. 3A is housed, and outside the closed space, a duct portion 51 of that air intake duct 50 is arranged.

In the foregoing first embodiment, the moving-direction duct portion 55 whose pipe-axis direction is substantially parallel to the moving direction Ds is provided as an example of a portion which is included in the air intake duct 50 and housed in the closed space S of the rotating drum 20, and whose pipe-axis direction has a component parallel to the moving direction Ds in which the mold 21 is moving at the central position C53a of the suction opening 53a (in claim 1, represented as a "portion"). However, the invention is not limited thereto as long as the pipe-axis direction has a component parallel to the moving direction Ds. For example, the pipe-axis direction may be inclined slightly with respect to a direction parallel to the moving direction Ds.

in the foregoing embodiment, a pulp fiber 2 is provided as a liquid absorbent material. However, as long as the material has a function to absorb liquid and the material disperses with being entrained in the air 3, the invention is not limited to liquid absorbent fiber such as the pulp fiber 2. Any other materials can be employed.

Reference Signs List 1 absorbent body, 2 pulp fiber (liquid absorbent material), 3 mixed air (air), 4 sheet-like member, 10 manufacturing apparatus, 10b manufacturing apparatus, 10c manufacturing apparatus, 20 rotating drum (mold member), 20a outer circumferential face (predetermined face), 21 mold, 21a bottom section, 22 suction hole, 24 roller, 25 circular wall (partitioned-space-forming member), 25a inner wall, 26 cylindrical wall, 27 partition wall, 31 supply duct, 31a supply opening, 41 air intake duct, 43a suction opening, 50 air intake duct, 51 outside-rotating-drum duct portion, 52 inside-rotating-drum duct portion, 53 suction box, 53a suction opening, 53d wall, 53u wall, 53s wall, 53eL left edge, 53eR right edge, 53ed downstream edge, 53eu upstream edge, 55 moving-direction duct portion (portion), 55a pipe end, 55b pipe end, 55c lid member, 57 width-direction duct portion, 57a pipe end, 57b pipe end, 58 bending section, 59 constricted section, 60 air intake duct, 62 inside-rotating-drum duct portion, 63 suction box, 63a suction opening, 63b lower end, 65 vertical-direction duct portion (portion), 65a pipe end, 65b pipe end, 65c lid member, 67 width-direction duct portion, 67b pipe end, 68 bending section, S closed space, Z1 first zone, Z2 second zone

The invention claimed is:

1. A manufacturing apparatus for an absorbent body, comprising:
a mold member that includes a mold formed in a depressed shape on a predetermined face and moves the mold along a first direction intersecting a width direction of the predetermined face;
a supply duct that is arranged at a predetermined position in the first direction and supply air towards the predetermined face from a supply opening, the air containing a liquid absorbent material;
a partitioned-space-forming member that is disposed at a position opposite to the supply opening with the predetermined face in between, and that forms a partitioned closed space together with the predetermined face; and
an air intake duct that sucks air in the closed space from a suction opening in order to set a pressure in the closed space to negative pressure, wherein
when the mold passes a position of the supply opening, the air in the supply duct is sucked from a suction hole of a bottom section of the mold to the closed space and the liquid absorbent material in the air is deposited into the mold, and thereby the absorbent body is formed,
the suction opening of the air intake duct is arranged opposite to the predetermined face in the closed space, and
concerning at least a portion that is included in the air intake duct and is housed in the closed space, a central-axis direction of the portion has a component parallel to a moving direction in which the mold is moving at a central position of the suction opening.

2. A manufacturing apparatus for an absorbent body according to claim 1, wherein
a negative pressure source is included outside the closed space,
the negative pressure source is connected to the portion from the width direction with a pipe in between,
between the portion and the suction opening, a bending section is disposed, the bending section being formed by bending a central-axis direction of the pipe in a virtual plane that intersects with the width direction.

3. A manufacturing apparatus for an absorbent body according to claim 2, wherein
the first direction is perpendicular to the width direction,
between the portion and the suction opening, a bending section is disposed, the bending section being formed by bending the central-axis direction of the pipe in a virtual plane that is perpendicular to the width direction.

4. A manufacturing apparatus for an absorbent body according to claim 2, wherein
concerning a section of the air intake duct between the bending section and the suction opening, a central-axis direction of the section does not have a component in the width direction.

5. A manufacturing apparatus for an absorbent body according to claim 1, wherein
the central-axis direction of the portion does not have a component in the width direction.

6. A manufacturing apparatus for an absorbent body according to claim 1, wherein
a negative pressure source is included outside the closed space,
the negative pressure source is connected to the portion from the width direction with a pipe in between,
the portion is formed extending towards a direction parallel to the moving direction,
the portion is connected to a duct portion from the direction parallel to the moving direction, the duct portion including the suction opening,
a central-axis direction of the duct portion does not have a component in the width direction.

7. A manufacturing apparatus for an absorbent body according to claim 1, wherein
the closed space includes, along the first direction, a plurality of positions at which the air intake duct can be installed opposite to the supply opening,
among the plurality of installable positions, the suction opening of the air intake duct is placed in at least a most upstream position in the first direction.

8. A manufacturing apparatus for an absorbent body according to claim 1, wherein
the mold member is a rotating drum that continuously rotates in a circumferential direction that serves as the first direction,
the mold is formed in a depressed shape at a predetermined interval in the circumferential direction on an outer circumferential face of the rotating drum, the outer circumferential face serving as the predetermined face, and
a pair of circular walls that covers openings of both ends of the rotating drum in the width direction is included as the partitioned-space-forming member, and the closed space is partitioned on an inner circumferential side of the rotating drum.

9. A manufacturing apparatus for an absorbent body according to claim 1, wherein
between the portion and the suction opening, a constricted section whose pipe is constricted in the width direction is disposed.

10. A manufacturing apparatus for an absorbent body according to claim 1, wherein
the suction opening is arranged opposite to the supply opening of the supply duct with the predetermined face in between.

11. A manufacturing method for an absorbent body, comprising:
preparing a mold member that includes a mold formed in a depressed shape on a predetermined face and moves the mold along a first direction intersecting a width direction of the predetermined face, a supply duct that is arranged at a predetermined position in the first direction and supply air towards the predetermined face from a supply opening, the air containing a liquid absorbent material, a partitioned-space-forming member that is disposed at a position opposite to the supply opening with the predetermined face in between, and that forms a partitioned closed space together with the predetermined face, an air intake duct that sucks air in the closed space from a suction opening in order to set a pressure in the closed space to negative pressure;

forming the absorbent body by a process in which, when the mold passes a position of the supply opening, the air in the supply duct is sucked from a suction hole of a bottom section of the mold to the closed space and the liquid absorbent material in the air is deposited into the mold, wherein the suction opening of the air intake duct is arranged opposite to the predetermined face in the closed space, concerning at least a portion that is included in the air intake duct and is housed in the closed space, a central-axis direction of the portion has a component parallel to moving direction in which the mold is moving at a central position of the suction opening.

\* \* \* \* \*